Jan. 1, 1974 M. TANTAU Plant Pat. 3,415
ROSE PLANT
Filed Nov. 12, 1972
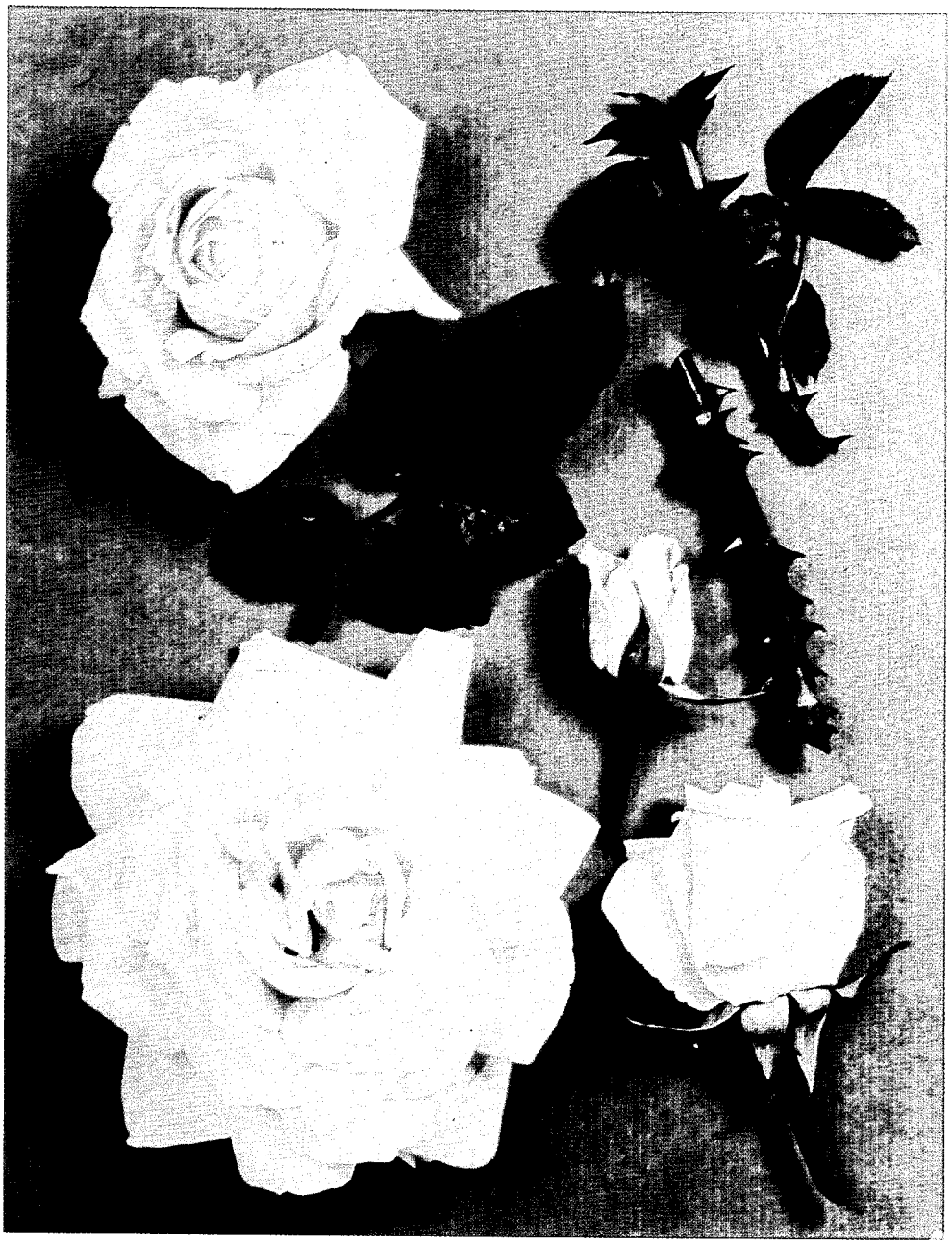
MATHIAS TANTAU
INVENTOR
BY
BUCKHORN, BLORE, KLARQUIST & SPARKMAN
ATTORNEYS

United States Patent Office

Plant Pat. 3,415
Patented Jan. 1, 1974

3,415
ROSE PLANT

Mathias Tantau, Schliebfach, Germany, assignor to Jackson & Perkins, Medford, Oreg.

Filed Nov. 12, 1971, Ser. No. 198,484
Int. Cl. A01h 5/00
U.S. Cl. Plt.—15 1 Claim This invention relates to a new and distinct variety of rose plant of the hybrid tea class originated by crossing the rose variety known as Piccadilly with the variety known as Königin der Rosen.

The primary object of this breeding was to produce a new and improved variety of the hybrid tea class bearing large deep yellow nonfading blooms for use as a garden rose.

This objective was fully achieved along with other desirable improvements as evidenced by the following unique combination of characteristics which are outstanding in the new variety and which distinguish it from its parents as well as from all other varieties of which I am aware:

(1) A large flower, measuring usually about 5" in diameter when fully open.
(2) An ovoid, pointed bud of a color very near Buttercup Yellow (Wilson's Horticultural Color Chart.)
(3) Bud and flower form similar to the variety Peace, U.S. Plant Pat. 591, but having no similarity in color.
(4) A vigorous bush whose main basal canes grow in an upright habit but whose side branches or laterals grow at a wide angle producing a plant of somewhat spreading as well as upright habit.
(5) Dark green medium large foliage with a good degree of resistance to powdery mildew.

Asexual reproduction of my new variety by budding, as performed at Uetersen, W. Germany and at Wasco, Calif., U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new rose variety, with color terminology in accordance with *Wilson's Horticultural Color Chart*, except where a general color term of ordinary dictionary significance is indicated.

Parentage: Seedling.
*Seed parent.*—Piccadilly.
*Pollen parent.*—Köningen der Rosen.

Classification:
*Botanic.*—Rosa hybrid.
*Commercial.*—Hybrid tea.

FLOWER (Observations were made in the afternoon in mid-July at Tustin, California.)

Blooming habit: Recurrent—continuous.

Bud:
*Size.*—1¼" to 1½" when petals start to unfurl.
*Form.*—Pointed, ovoid.
*Color.*—When sepals first divide—very near Buttercup Yellow (5). When half blown—inside of petals, color lightens slightly to Lemon Yellow (4); reverse of petals, Lemon Yellow (4/1)—slightly lighter than upper side.
*Sepals.*—Color: Outside: Lettuce Green (861/1), overlaid on side exposed to sun with Oxblood Red (00823/3). Inside: Covered with white tomentum. Three appendaged sepals *lightly appendaged*. Two unappendaged sepals hairy edged.

*Receptacle.*—Color: Lettuce Green (861/1). Shape: Funnel, very prominent. Size: Large. Surface: Smooth.
*Peduncle.*—Length: Medium. Surface: Prickly. Color: Lettuce Green (861/1), overlaid with shadings of Oxblood Red (00823/3) on exposed side. Strength: Stiff, erect.
*Opening.*—Flower opening habit is similar to variety Peace, U.S. Pl. Pat. 591.

Bloom:
*Size.*—Large—average size when fully expanded (5").
*Borne.*—Singly, occasionally several together.
*Stems.*—Medium.
*Form.*—When first open—high center. Permanence—retains its form to the end.
*Petalage.*—Petals curl only slightly, about 37.
*Color.*—Center of flower: Upper side of petals—Chrome Yellow (605). Reverse side of petals—slightly lighter than Chrome Yellow (605/1). Outer petals: Upper side of petals—same as center petals. Reverse of petals: Same as center petals. Base of petals: Intensity increases to Buttercup Yellow (5) at base end of petal. General tonality from a distance—Chrome Yellow (605). No variegations.
*Discoloration.*—General tonality at end of first day—same as newly opened. Third day—older flowers slightly overcast with tints of rose after exposure to sun. Yellow color lightened to Lemon Yellow (4/2).
*Fragrance.*—Slight.

Petals:
*Texture.*—Thick.
*Surface.*—Inside—satiny. Reverse—satiny.
*Shape.*—Broadly oval.
*Form.*—Edges slightly curled.
*Arrangement.*—Loosely imbricated.
*Petaloids in center.*—Few.
*Persistence.*—Drop off cleanly.
*Lastingness.*—On the plant—long. As cut flower—long.

Reproductive parts:
*Stamens, anthers.*—Large, many; arrangement mixed with petaloids. Color—yellow.
*Stamens, filaments (threads).*—Medium. Color—yellow.
*Pollen.*—Color—lemon yellow.
*Styles.*—Loosely separated, of uneven lengths, thin.
*Stigmas.*—Color—red.
*Ovaries.*—All enclosed in calyx.

PLANT

Form: Bush.
Growth: Vigorous; upright; branching.
Foliage: Compound of 5 leaflets.
*Size.*—Large.
*Quantity.*—Normal.
*Color.*—New foliage: Near Oxblood Red (00823) before unfolding. Old foliage: Near Parsley Green (00962) upper side; near Willow Green (000862) lower side.
*Leaflets:* Shape—broadly oval. Texture—upper side, leathery—under side, smooth—Ribs and veins, ordinary. Edge—serrated. Serration—single; small. Petiole—Rachis—color; green below, reddish on top. Under side—large prickles; small prickles on top.
*Stipules.*—Long, green in contrast to reddish petiole; nearly smooth with very small glands.
*Disease resistance.*—Resistant to mildew under normal growing conditions at Irvine, Calif.

Wood:

*New wood.*—Color—light green, Scheeles Green (860/2) on shaded side; reddish on sunny side.

*Bark.*—Smooth.

*Old wood.*—Color—Scheeles Green (860) to (860/1) on shaded side; brown on exposed side. Bark—smooth.

Thorns:

*Quantity.*—On main stalks from base—many. On laterals from stalk—many.

*Form.*—Narrow base; hooked downward.

*Color when young.*—Green, lighter than (860/3) overlaid with tints of light brown.

*Position.*—Irregular.

*Prickles.*—Quantity: On main stalks—few; on laterals—few. Color: Brown.

*Short Needles.*—Quantity: On main stalks—none. On laterals—none.

I claim:

1. A new and distinct variety of rose plant of the hybrid tea class, substantially as herein shown and described, characterized particularly as to novelty by the unique combination of a vigorous, upright but branching plant, leathery foliage, ovoid pointed bud of Buttercup Yellow (Wilson) fading very little as the flower opens and holding open form and color for several days on the plant.

No references cited.

ROBERT E. BAGWILL, Primary Examiner